United States Patent [19]

Cabrera et al.

[11] Patent Number: 4,896,546
[45] Date of Patent: Jan. 30, 1990

[54] LIQUID METERING AND TRANSFER VALVE ASSEMBLY

[75] Inventors: Pedro P. Cabrera; Daniel A. Estoque, both of Miami, Fla.

[73] Assignee: Coulter Electronics, Inc.

[21] Appl. No.: 296,905

[22] Filed: Jan. 11, 1989

Related U.S. Application Data

[63] Continuation of Ser. No. 113,297, Oct. 26, 1987, abandoned.

[51] Int. Cl.$^4$ ............................................. G01N 1/00
[52] U.S. Cl. ................................................. 73/863.73
[58] Field of Search .......... 73/863.71, 863.72, 863.73, 73/864.21, 864.83, 864.84; 422/103

[56] References Cited

U.S. PATENT DOCUMENTS

| | | | |
|---|---|---|---|
| 3,567,390 | 3/1971 | Rothermel | 422/103 |
| 4,152,391 | 5/1979 | Cabrera | 422/103 |
| 4,445,391 | 5/1984 | Cabrera | 73/864.12 |
| 4,507,977 | 4/1985 | Cabrera | 73/864.12 |
| 4,577,515 | 3/1986 | Sonneya et al. | 73/863.73 |
| 4,702,889 | 10/1987 | Cabrera et al. | 422/103 |
| 4,726,237 | 2/1988 | Yung | 73/863.73 |
| 4,756,201 | 7/1988 | Uffenheimer | 73/864.83 |

*Primary Examiner*—Robert R. Raevis
*Attorney, Agent, or Firm*—Sidney N. Fox; Gerald R. Hibnick

[57] ABSTRACT

A rotary liquid metering and transfer valve assembly for a diluting system which includes a pair of stationary valve disc elements sandwiching a central, rotatable valve disc element, said disc elements being coaxially aligned and mounted on a spindle. One of the outer stationary elements has a first external loop secured thereto, said loop having a precise interior volume. An aspirator probe is secured to the other of said stationary elements. The central element has formed therein an axial segmenting passageway having a precise interior volume. A second external loop is secured to the center element. The second loop extends outwardly, preferably radially, of said element and has a precise interior volume. Appropriate interior passageways are provided in the outer elements for directing a liquid sample in a continuous path through the valve assembly, the path including the one segmenting passageway and the first and the second external loops. Additional interior passageways also are provided for coupling the valve assembly to sources of diluent and to exterior destinations. The central element is rotated to isolate the contents of the segmenting passageway and of the first and the second external loops and diluent is fed thereto to drive the isolated contents to said destinations. Only a single loading step is required to obtain three precise volumes of liquid sample. The valve assembly can be rinsed and continuous internals channels are provided for preventing any liquid from reaching the circumferential surface of the valve assembly.

12 Claims, 3 Drawing Sheets

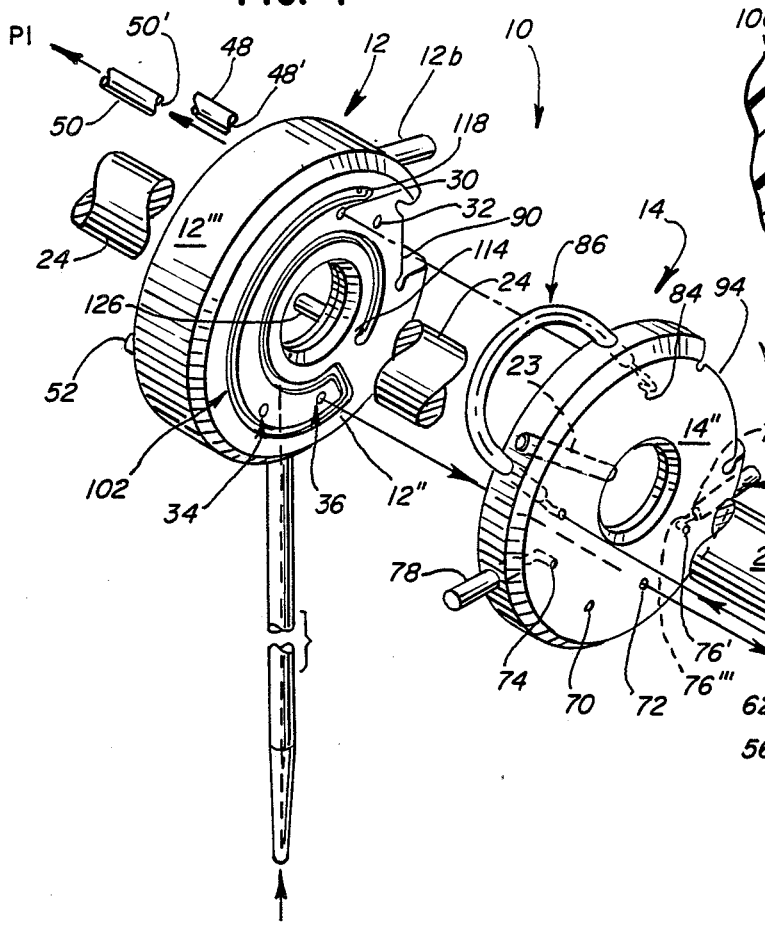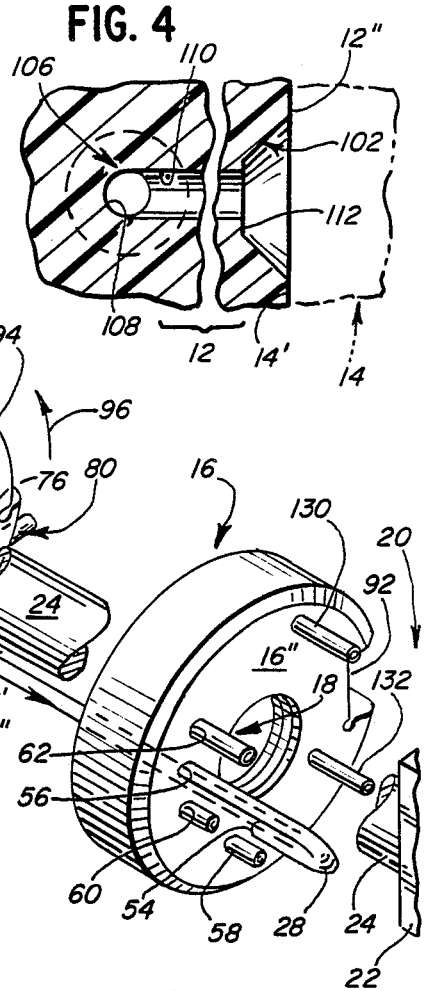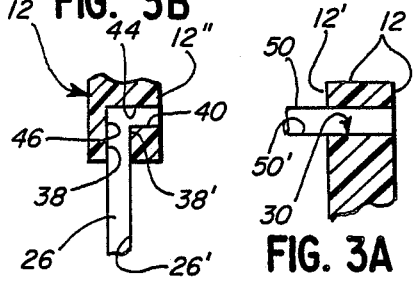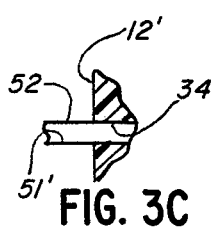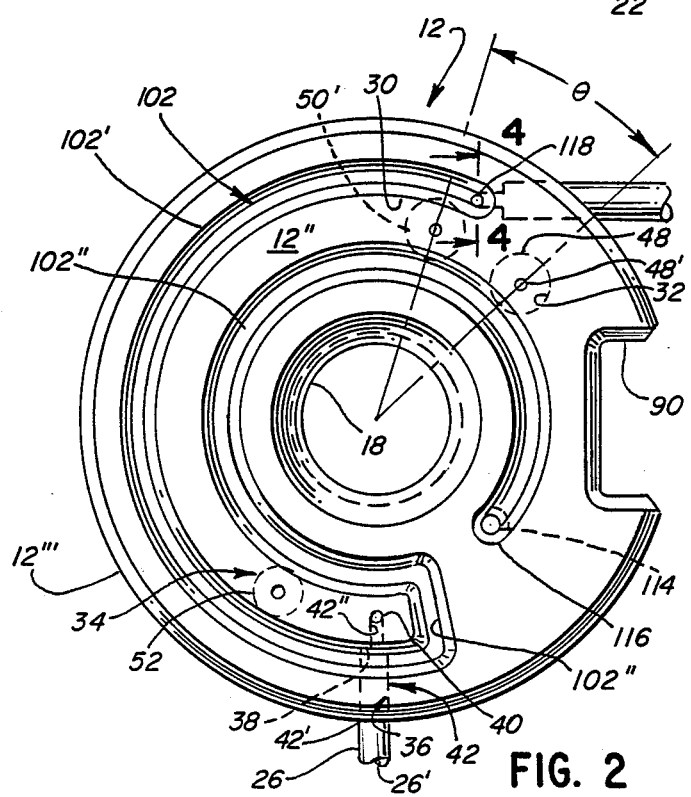

LIQUID METERING AND TRANSFER VALVE ASSEMBLY

This application is a continuation of application Ser. No. 113,297 filed Oct. 26, 1987 now abandoned.

CROSS-REFERENCE TO RELATED PATENTS AND APPLICATIONS

Reference is made to the following patents and patent application, each owned by the assignee of this application.

U.S. Pat. No. 4,152,391 granted on May 1, 1979
U.S. Pat. No. 4,445,391 granted on May 1, 1984
U.S. Pat. No. 4,507,577 granted on Apr. 1, 1985
U.S. patent application Ser. No. 819,381 filed Jan. 16, 1986 by Pedro Pablo Cabrera, H. Antonio Berra and Edward Doty.

The disclosures of the above identified patents and the patent application identified above are hereby incorporated by reference herein for the purpose of providing background of the herein invention.

BACKGROUND OF THE INVENTION

This invention relates generally to liquid metering and transfer valves for use in a diluting system and more particularly provides a liquid metering and transfer valve assembly of the rotary type for measuring and delivering at least three precise microliter volumes of a liquid sample along with respective predetermined volumes of a diluent to different preselected destinations and employing a single aspiration or loading step.

Reference has been made to U.S. Pat. Nos. 4,445,391 and 4,152,391. The liquid transfer valves provided in these patents preferably comprise a pair of stationary valve disc elements sandwiching a center rotatable valve disc element, said elements arranged coaxially with the faces of the center element frictionally sealingly engaged with the adjacent faces of the stationary elements. These valves have achieved considerable commercial success and included internal passageway means of precise interior volume to provide a precise volume of a single liqud sample for dilution. The segmenting passageway means were provided in the center, movable valve disc of the valve assembly. In both patents there was provided an external loop to provide a precise volume of liquid sample different from the measured volume provided by the interior segmenting passageway means. In the valve of U.S. Pat. No. 4,152,391, the external loop was connected to the center movable valve disc element and passed through a suitable slot formed in one of the stationary valve disc elements so that the center valve disc element could be rotated. In the valve of U.S. Pat. No. 4,445,391, the external loop was connected to one of the stationary valve disc elements and coupled to second passageway means formed in the center valve disc element. In both patented valve assemblies, external connections for feed of diluent and for coupling to lines leading to predetermined locations or destinations were made to the outer, stationary valve disc elements of said valve assemblies. The valve assembly of the U.S. Pat. No. 4,152,391 also required interior galleries to define several of the liquid paths therethrough.

The valve assembly of the U.S. Pat. No. 4,445,391 was less complex in construction than that of the U.S. Pat. No. 4,152,391, providing the external loop coupled in series with the segmenting passageway means rather than parallel thereto. This meant that the loading step of the valve assembly of the U.S. Pat. No. 4,152,391, particularly if three dilutions were desired required a Y path or at least two aspiration steps during the loading condition. The U.S. Pat. No. 4,445,391 valve assembly was less costly to manufacture than the valve assembly of the U.S. Pat. No. 4,152,391. Sample volume was reduced. Interior galleries found in the U.S. Pat. No. 4,152,391 were eliminated in the U.S. Pat. No. 4,445,391 valve assembly. Of advantage with the U.S. Pat. No. 4,152,391 valve assembly was the provision of means whereby a dilution, in addition to the two dilutions provided by the U.S. Pat. No. 4,445,391 valve assembly, could be provided, although the sampling paths provided for the second and third liquid sample volumes were in parallel and the valve assembly required a pair of arcuate slots in the one stationary valve disc element and further required a pair of internal gallery formations. More important, the third volume could not be obtained during the same aspiration or loading step and required a "one/or the other" selection. The two patented valve assemblies were appreciably different in structure so that one could not convert one structure into the other without substantial change nor could one structure be replaced with the other without change in operation of the instrument. The valve assembly of the U.S. Pat. No. 4,445,391 could not be remodeled by following the teachings of U.S. Pat. No. 4,152,391 in an effort to provide three measured volumes of liquid sample for forming three dilutions without drastic and uneconomical alterations in the structure of the U.S. Pat. No. 4,445,391 valve assembly. Capability of retrofit of a valve assembly capable of providing three dilutions on a single loading in instruments in which the U.S. Pat. No. 4,445,391 valve assembly is installed would be of considerable advantage.

Accordingly, it has become desirous to provide for delivery of three separate dilutions from a single valve assembly without drastic alterations of the structure of the U.S. Pat. No. 4,445,391, to provide therein means defining a series path through the valve assembly to enable use of a single aspiration or loading step to introduce liquid sample through all the measuring portions of the valve assembly and yet to retain all the advantages of the U.S. Pat. No. 4,445,391 patented valve assembly.

Further, it would be of considerable advantage, notwithstanding the paucity of available space, to incorporate in a valve assembly capable of providing three dilutions, means to prevent any material from escaping from any internal passageway junctions and traveling to the outer circumferential surface of the valve assembly.

SUMMARY OF THE INVENTION

A rotary operating liquid metering and transfer valve assembly for use in a diluting system, said valve assembly including means defining at least three measuring chambers arranged in series communication with a single source of liquid sample, one of said measuring chambers constituting internal segmenting passageway means. The second of said metering chambers comprises a first external loop of precise interior volume and the third of said measuring chambers comprising a second external loop of precise interior volume. The valve assembly comprises a pair of stationary valve disc members having a central rotatable valve disc sandwiched therebetween, said disc members being arranged axially aligned with the opposite faces of the central valve disc frictionally sealingly engaged with the facing surfaces of the next adjacent stationary valve discs. The first external loop is connected to one of the stationary valve discs and is arranged to be placed in communication with the segmenting passageway means. The second external loop is connected to the circumferential surface of the central valve disc and extends outwardly thereof, preferably radially thereof. A second set of passageways are formed in the central valve disc communicating with said second external loop and adapted to be placed in communication with said first external loop. A sampling or aspiration probe is connected to the other stationary valve disc and arranged to be placed in communication with the segmenting passageway means. Suitable passageways and conduit means are provided to couple each of the measuring chambers to a source of diluent and further to direct the said volume of diluent and the associated volume of liquid sample to different exterior locations for testing purposes, thereby providing three dilutions to respective preselected exterior locations.

Additionally, the invention provides a liquid metering and transfer valve assembly capable of providing three liquid sample dilutions, the valve assembly including a pair of stationary valve disc elements sandwiching a coaxially arranged central movable valve disc element, the facing surfaces being frictionally engaged, means in at least one frictionally engaged surface capable of preventing liquids from flowing from the junctions of internal passageways along the facing frictionally engaged surfaces to the circumferential surface of said valve assembly.

BRIEF DESCRIPTION OF THE DRAWINGS:

FIG. 1 is an exploded, diagrammatic, isometric representation of the liquid metering and transfer valve assembly constructed in accordance with the invention herein and illustrated in the aspiration or load condition;

FIG. 2 is an enlarged elevational view of the inner face of one of the stationary valve disc members of the valve assembly illustrated in FIG. 1;

FIGS. 3A, 3B and 3C are fragmentary diagrammatic sectional details illustrating some of the passageways carried by the stationary valve disc member of FIG. 2;

FIG. 4 is a fragmentary enlarged sectional detail taken along line 4—4 of FIG. 2 and viewed in the direction of the arrows;

DESCRIPTION OF PREFERRED EMBODIMENT

Figures 5, 6:
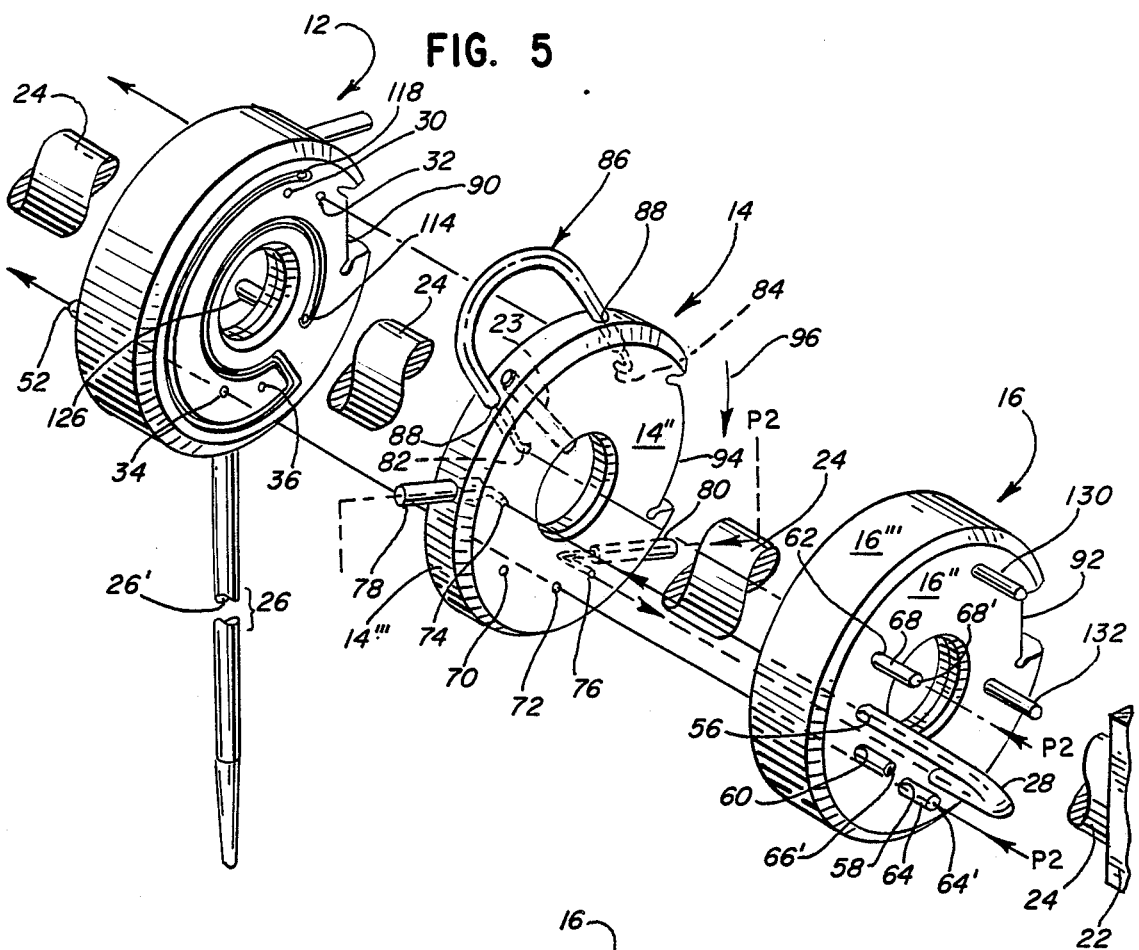
FIG. 5 is an exploded, diagrammatic, isometric representation of the liquid metering and transfer valve assembly according to the invention and illustrated in the condition assumed during the delivery of the measured volumes.
FIG. 6 is an enlarged view of the other stationary valve disc member as shown in FIG. 5 illustrating the inner face thereof.

The invention herein is intended to provide a liquid metering and transfer valve assembly of the rotary type for use in a diluting system, said valve assembly having the capability of providing at least three discrete precisely measured volumes of a liquid sample employing a single loading or aspiration step and delivering said volumes, each accompanied by a preselected volume of diluent, to preselected destinations or locations. The said valve assembly has the capability of being retrofit into commercially available systems and, of importance, can be constructed without drastic changes in the structure and operation of at least one widely used commercially available prior valve structure. In order to appreciate the improvements provided by the herein described invention, a brief review of the prior patented valve assembly structures is in order.

The liquid metering and transfer valve assembly disclosed in the referenced U.S. Pat. No. 4,445,391 was capable of delivering from a single liquid sample source, simultaneously, two different, precisely measured volumes of liquid sample with a predetermined volume of diluent, as two dilutions, respectively delivered to a pair of different exterior locations for testing purposes or the like. The liquid metering and transfer valve assembly according to the present invention is provided with means for measuring and delivering an additional precisely measured volume of liquid sample from the same source, along with a preselected volume of diluent to an exterior location, and incorporates said last mentioned means without drastic change being required to be made to the commercially employed valve assembly disclosed in the U.S. Pat. No. 4,445,391. According to the herein invention, said last mentioned means comprises a second external loop having a precise interior volume which is secured to the center movable valve disc element and projects outwardly, preferably radially, therefrom and suitable internal passageways being formed in said valve assembly for coupling said second external loop in series relationship with the segmenting passageway means and first external loop.

As described, the referenced patented liquid metering and transfer valve assembly is capable of measuring and delivering, from a single liquid sample source, two precise volumes of sample, along with preselected volumes of diluent, as two dilutions, to preselected exterior destinations or locations. Suitable conduit means are coupled to said valve assembly to direct the precise liquid sample volumes and associated volumes of diluent to said destinations. Sets of internal passageways are provided for establishing two fluid paths within the valve assembly, one set defining paths for traversal by preselected volumes of diluent and the other set being defined for traversal in series coupled relationship with measuring chambers within said valve assembly, each measuring chamber having a precise volume. One of the measuring chambers is provided by segmenting passageway means formed in a movable one of the valve elements while the other of said chambers is defined by a hollow, external first loop of precise interior volume secured to one or the other of the stationary valve elements of the valve assembly. The valve elements of said valve assembly are formed of a pair of stationary disc members sealingly engaged frictionally with an inner or center rotatable disc member sandwiched therebetween in coaxial relationship. The said valve assembly operates between a first or load condition during which a liquid sample is introduced from a source thereof by way of an aspirator probe driven by an exterior located aspirator pump, and a second or delivery condition. The aspirator probe is coupled to a valve element either directly or through a suitable conduit system. In the loading or aspirating condition, a continuous path is established between the aspirator probe, by way of the segmenting passageway means and the external loop through suitable connecting passageways provided within the valve assembly and leading to the aspirator pump by way of suitable exterior conduit means. The valve assembly is operated by rotating the center valve disc member to place same in the second or delivery condition, placing the volume segmented from the continuous path by the segmenting passageway means on rotation of said center valve disc member, into a path established to direct diluent thereto for delivery from the valve assembly to a preselected destination. Simultaneously, the volume of liquid sample contained in the external loop is coupled into a path through which diluent is introduced to sweep said volume from the second measuring chamber to a preselected destination.

The valve assembly of referenced U.S. Pat. No. 4,507,977 is similar to the valve assembly of U.S. Pat. No. 4,445,391 except that only one of the outer disc elements is stationary, the other valve disc element being rotatable and carries an additional aspirator probe, said valve assembly nevertheless being capable of delivering only two dilutions. The valve assembly of referenced U.S. Pat. No. 4,152,391 provides for measuring and delivering of three measured segments of liquid sample but its construction is drastically altered from the structures taught by the other referenced patents, requiring special slots and interior galleries.

In the valve assembly of the U.S. Pat. No. 4,445,391, the external loop is connected to a stationary one of the valve disc elements while, in contrast, the valve assembly of the U.S. Pat. No. 4,152,391 provides two external loops, each having a precise internal volume but both secured to the center rotatable valve element and each passes through arcuate slots provided in a stationary valve disc element. The last mentioned construction requires the establishment of parallel paths for loading with liquid sample. One loop measures the original sample while the other loop deals with a second sample source, i.e. a pre-diluted sample, not the original sample. Aspiration or loading of the measuring chambers of said valve assembly could not be performed from a single sample source in a single aspiration step.

Now referring to the drawings, the liquid metering and transfer valve assembly constructed in accordance with the herein invention is illustrated in FIGS. 1 through 8 and comprises an assembly 10 formed of a pair of coaxially arranged, outer stationary valve disc elements 12 and 16 having a rotatably movable central valve disc element 14 also coaxially arranged and sandwiched therebetween. The central valve disc element 14 is disposed so tat its opposite faces 14' and 14" are frictionally, sealingly engaged with the inner facing surfaces 12" and 16' of the stationary valve disc elements 12 and 16 respectively. Each of the valve disc elements 12, 14 and 16 have a central passageway 18 of the same inner diameter and all are mounted coaxially on a spindle 20, including spindle support 22 and the shaft 24. Pin 23 is fitted radially into the central valve disc element 14 to enter into the axial passageway 18 thereof so as to engage the shaft 24, the other valve disc elements remaining stationary.

In FIG. 1, the valve assembly 10 is illustrated in the aspiration or loading condition. The left hand element 12 carries an aspirator probe 26 while the right hand element carries one external hollow loop 28. A pair of axially parallel through passageways 30 and 32 are formed in stationary valve disc element 12. A third through axial passageway 34 is formed in said element 12 axially parallel to passageways 30 and 32 but angularly spaced therefrom. An angular passageway 36 is formed in the valve disc 12 opening at one end 38 to the outer circumferential surface 12''' of said element 12 and, at the opposite end 40, to the inner face 12" thereof. A line taken through the axial center of passageway 30 and the axial center of valve disc element 12 defines an angle Theta with a line taken through the axial center of passageway 32 and the axial center of said valve disc element 12. This is illustrated in FIG. 3. A line taken through the axial center of passageway 34 and the axial center of said element 12 and a line taken through the axial center of the radial portion 42 and the axial center of said element 12 define the same angle Theta. The radial portion 42 of passageway 36 has an inner end 38', said passageway 36 also being formed with an axial portion 44 having an inner end 46. The central axes of the passageway portions 42 and 44 define a right angle at their intersection. As is evident from FIG. 3, the distance between the axial center of passageway portion 44 and the axial center of passageway 34 is the same as the distance between the axial centers of passageways 30 and 32. The outer portion 42' of passageway portion 42 has a larger diameter than the inner portion 42 thereof to receive the aspirator probe 26 secured tightly sealingly therein. The aspirator probe 26 carries a central axial through bore 26'. Bore 26' is of the same internal diameter as the inner portion 42" of passageway portion 42 so that the junction of bore 26' and passageway portion 42 is flush, communicating with the inner end 46 of passageway portion 44 of angular passageway 36. Passageway portion 44 has the same internal diameter as the passageway portion 42".

Passageways 30, 32 and 34 all are of the same inner diameter and all receive hollow nipples 48, 50 and 52 tightly, sealingly secured respectively therein. Each of the nipples 48, 50 and 52 carry axial bores 48', 50' and 52' respectively. Each of said axial bores 48', 50' and 52' have the same inner diameter as the central axial bores of passageway portions 42" and 44 of angular passageway 36. All the nipples 48, 50 and 52 extend outward of the outer face 12' of the valve disc element 12. Passageways 30, 32, 34 and portion 44 of passageway 36 all have their central axes located at the radial distance from the axial center of valve disc element 12. The respective portions of the passageways and nipples are presented diagrammatically in the details of FIGS. 3A, 3B and 3C.

The right hand valve disc element 16 is provided with two pair of angularly spaced axially parallel through passageways, one pair constituted by passageways 54 and 56, the second pair constituted by passageways 58 and 62, each pair opening to opposite faces 16' and 16" of the valve disc element 16. Passageways 54 and 56 are formed of portions 54' and 56' opening to the outer face 16" and comprise the major portions of passageways 54 and 56. The inner ends of passageway portions 54' and 58' open to smaller diameter portions 54" and 56" respectively of passageways 54 and 56. Passageway portions 54" and 56" are coaxial with passageway portions 54' and 56' respectively and open to the inner face 16' of valve disc element 16. Passageway portions 54' and 54" are coaxial, passageway portions 56' and 56" also being coaxial. The external loop 28 has an inner diameter identical to the inner diameter of passageway portions 54' and 56". The ends 28' of external loop 28 are inserted tightly, sealingly for securement within passageway portions 54' and 56' respectively until they abut flush with the inner ends of passageway portions 54" and 56". The interior of loop 28 is uniform and has a precise volume.

The second pair of axially parallel passageways 58 and 62 have the same inner uniform diameter and open respectively to the inner facing surface 16' of the valve disc element 16. An additional axially parallel through passageway 60 is formed in the disc element 16 opening to the opposite faces 16' and 16" thereof. The inner diameter of passageway 60 is identical to the inner diameter of passageways 58 and 62. The axial center of passageway 62 is spaced from the axial center of passageway 56 by the same distance that the axial center of passageway 60 is spaced from the axial center of passageway 56. The distance between the axial centers of passageways 54 and 56 is the same as the distance between the axial centers of passageways 58 and 62. The axial centers of passageways 54, 56, 58, 60 and 62 all lie in a circle taken concentric with the axis of the disc 16. Identical nipples 64, 66 and 68 are tightly, sealingly secured within the respective passageways 58, 60 and 62, one end 64', 66' and 68' respectively extending outward the same distance from the outer face 16" of the valve disc element 16 with the respective opposite ends of said nipples being flush with the surface of face 16' of said valve disc element 16. The inner diameters of said nipples 64, 66 and 68 are identical.

Referring to FIGS. 1, 5, 7 and 8, the rotatable center valve disc element 14 is provided with a first pair of axially parallel through passageways 70 and 72, each having the same inner diameter. First and second angular passageways 74 and 76 also are formed in the center valve disc element 14, one end of each said angular passageway opening to the surface 14" of the valve disc element 14 with the opposite ends opening to the outer circumferential surface 14'" thereof. Angular passageway 74 comprises an axially parallel portion 74' extending inward of the face 14", a radial portion 74" extending from the outer circumferential surface 14'" of the valve disc element 14 inward toward the axis of said valve disc element and a second radial portion 74'" coaxial with portion 74" and communicatively linking the inner end of portion 74' with radial portion 74" to define generally a right angle. The axial centers of axial portion 74' of passageway 74 and the passageway 70 are spaced apart the same distance as between passageways 58 and 60 formed in the valve element 16.

Angular passageway 76 comprises an axially parallel portion 76' extending inward of the face 14', a radial portion 76" extending inward from the outer circumferential surface 14'" of said valve disc element 14 and a second radial portion 76'" coaxial with the portion 76" and communicatively linking portions 76' and 76" to define a generally right angle. Portion 74" opens to said outer circumferential surface 14'" of said valve disc element 14 at a location opposite but displaced from a line taken axially through portions 76" and 76'" of passageway 76, said line being parallel to a line taken axially through passageway portions 74" and 74'" of passageway 74. The center axes of passageways 70 and 72 are located at the same radial distance from the axis of valve disc element 14 and lie along a circle taken concentric to the said axis. Likewise, the center axes of the axial passageway portions 74' and 76' lie in same concentric circle. The center axes of the radial portion 76' of passageway 76 and passageway 72, and the center axes of the passageways 70 and 72 are spaced apart the same distance as passageways 54 and 58, 60 and 56, and 56 and 62 of valve element 16. The inner diameters of passageway portions 74', 74'", 76' and 76'" are the same. Nipples 78 and 80 are seated sealingly, tightly secured fully within passageway portions 74" and 76" respectively of angular passageways 74 and 76, said nipples having uniform axial bores each having an inner diameter matching the inner diameter of passageway portions 74'" and 76'" respectively.

A second pair of angular passageways 82 and 84 also are formed in the center valve disc element 14. Angular passageway 82 comprises axially parallel passageway portion 82' leading inward from the surface of face 14", radial passageway portion 82" opening to the outer circumferential surface 14'" of valve disc element 14 and radial passageway portion 82'" coaxial with portion 82" and extending toward the axis of center valve disc element 14 until intersecting communicatively with the innermost end of passageway portion 82' to define a generally right angle therewith. Angular passageway 84 comprises axially parallel portion 84' opening to the face 14' of valve disc element 14, radial passageway portion 84" opening to the outer circumferential surface 14'" of valve disc element 14 and radial passageway portion 84'" coaxial with radial passageway portion 84" and linking same communicatively with the innermost end of axial passageway portion 84' to define a generally right angle therewith. The inner diameters of passageway portions 82', 82'", 84' and 84'" are the same. The axes of passageway portions 82' and 84' are parallel, the axis of passageway portion 82' intersecting the same concentric circle as the axes of passageways 70 and 72 and passageway portions 74' and 76'. The axial centers of passageway portions 82' and 84' are spaced the same distance as are spaced the axial centers of passageways 54 and 56, and the axial centers of passageways 58 and 62 of valve disc element 16. Further, the axial center of passageway portion 82' is spaced from the axial center of passageway portion 74' the same distance as passageway 72 is spaced from passageway 70, and the same distance as the spacing between axial centers of passageways 54 and 58 of valve disc element 16 as viewed in FIGS. 5 and 6. A second hollow external loop 86 has its ends 88 seated fully sealingly, tightly secured within passageway portions 82" and 84" so as to abut the passageway portions 82'" and 84'" respectively. The loop 86 has a uniform axial bore therein of the same internal diameter as that of passageway portions 82', 82'", 84' and 84'", the external loop 86 having a precise interior volume The loop 86, if desired, may have an interior volume different from the interior volume of loop 28.

The stationary valve disc elements 12 and 16 are provided with circumferential notches 90 and 92 while the center valve disc element 14 is provided with a circumferential notch 94 of the same depth as notches 90 and 92 but encompassing a greater angular distance along the circumferential opening length than the angular opening extent of the circumferential notches 90 and 92. When the valve disc elements 12, 14 and 16 are mounted coaxially on the shaft 24 of spindle 20, the notches 90 and 92 are aligned, the opposite sides of said notches serving to limit the extent of the relative angular rotation of the center valve disc element 14 to an angular distance equal to the difference between the angular length of aligned notches 90 and 92 and the angular length of the notch 94. The angular rotation of the center valve disc element 14 which is required to change the valve assembly 10 from one condition (or operating mode) to the other condition (or operating mode) is represented by the arrow 96 in the FIGS. 1, 5 and 7, and here is 30°. When the valve disc elements 12, 14 and 16 are assembled to constitute the valve assembly 10, all of the axially directed passageways and passageway portions which are to communicate with the other passageways and passageway portions carried by the valve disc elements are coaxial during one or the other of the modes of operation, as shown in the respective FIGURES of the drawing. All of said axially directed passageways and the portions of passageways are parallel to the common center axes of the valve disc elements.

The valve assembly 10 operates between three conditions or modes of operation, the first being the aspiration or loading condition, the second being the delivery condition and the third being the backwash or rinse condition. The relative relationship of the valve disc elements assumed during the loading and the backwash conditions are identical. The arrangement of the said valve disc elements in the various conditions and the flow paths are illustrated in the FIGURES; the loading condition being illustrated in FIG. 1, the delivery condition being illustrated in FIG. 5 and the backwash or rinse condition being illustrated in FIG. 7.

The stationary valve disc element 12 carries passageways which function to communicate between the measuring portions of the valve assembly 10 and the exterior destinations or locations, including the liquid sample source, a pair of destination locations intended to receive the measured quantities of liquid sample and associated preselected volumes of diluent, an exterior source of diluent and an exterior located aspirator pump P1 which hydraulically drives the liquids through the valve assembly 10 during the loading condition of the valve assembly.

The other stationary valve disc element 16 also carries communicating passageways defining portions of the liquid paths through the valve assembly 10 but, in addition, carries one of the measuring portions of the valve assembly 10, namely the external hollow loop 28. Passageways 58, 60 and 62 carried by the valve disc element 16 are coupled by suitable conduit means (not shown) to selected exterior diluent dispenser means (not shown). Of these passageways, only passageways 58 and 62 function to introduce diluent to the valve assembly 10 during the delivery mode of operation. Passageway 60 is employed to introduce diluent to the valve assembly 10 only during the backwash or rinse mode of operation to be described hereinafter.

The rotatable center valve disc element 14 carries the segmenting passageway means, namely passageway 72, for providing one of the measured volumes of liquid sample, and additionally carries the third measuring portion of the valve assembly 10, namely, the second external loop 86. In addition to carrying the aforementioned two measuring portions, the center valve disc element carries a pair of angular passageways, one, 74, of which is capable of being coupled by suitable conduit means (not shown), to an exterior destination or location and the other, 76, being coupled to another diluent dispenser (not shown) for delivering a preselected volume of diluent to drive one measured volume of liquid sample trapped in loop 28 to the last mentioned exterior destination or location.

As mentioned, FIG. 1 illustrates the valve assembly 10 in the condition assumed during the loading or aspiration condition or mode of operation during which the measuring portions of the valve assembly 10 are disposed to define a single continuous series path between the aspirator probe 26 on one hand and the aspirator pump P1 on the other. Thus, the continuous path is defined from the liquid sample source and aspirator probe 26 via passageway 36 to and through passageway 72, to and through passageway 82, to and through passageway 56, to and through loop 86, to and through passageway 84 to passageway 30 and from there, via suitable conduit means (not shown), to the aspirator pump P1.

When the valve disc element 14 is rotated through the angle Theta (30°) required to change the valve assembly 10 from the aspiration (or loading) condition or mode of operation illustrated in FIG. 1 to the delivery condition or mode of operation illustrated in FIG. 5, there are three distinct paths defined through the valve assembly 10, each leading to suitable exterior conduit means (not shown) which respectively lead to the three destination locations for delivery of the measured volumes of liquid sample plus selected volumes of diluent thereto. The through segmenting passageway 72, defining the smaller measuring portion, has been rotated to place it out of the first mentioned path, carrying its captured volume of liquid sample into a first delivery path along which said volume is transferred to the first exterior destination location along with a preselected volume of diluent from a diluent dispenser (and diluent source) located exterior of the valve assembly and coupled to said first path by suitable conduit means (not shown). The first delivery path extends from the diluent dispenser (not shown) to and through passageway 58, to and through segmenting passageway 72, to and through passageway 34 from which it is directed to the first exterior destination (not shown).

In the delivery condition of the valve assembly 10, as shown in FIG. 5, a second path is established for delivery of the second measured volume of liquid sample from the second measuring portion, the external loop 28, this volume being isolated from the continuous measuring path defined during the loading condition for transfer along the second delivery path, ultimately to the second destination location (not shown) along with a preselected volume of diluent delivered to said delivery path through suitable conduit means (not shown) from an exterior located diluent dispenser (not shown) and diluent source (not shown) coupled to passageway 76. The second delivery path continues from passageway 76 to and through passageway 54, to and through loop 28, to and through passageway 56, to and through passageway 74 and from there, to the second exterior destination or location via suitable conduit means (not shown). The second delivery path is independent of the first delivery path described above and a third delivery path through the valve assembly 10 which will be described hereinafter.

The third delivery path through the valve assembly 10 which is defined when the said assembly is placed in the delivery condition and is coupled between a diluent dispenser (not shown) and a third exterior destination location (not shown) to deliver the measured volume of liquid sample trapped in loop 86 when the valve disc element 14 is rotated to the delivery condition. This third delivery path leads from the diluent dispenser (not shown) via suitable conduit means (not shown), to and through passageway 62, to and through passageway 82, to and through the loop 86, to and through passageway 84, via suitable conduit means (not shown) to and through passageway 32 and thence is directed to the third exterior destination location via suitable conduit means (not shown) along with a preselected volume of diluent received from the diluent dispenser (not shown). Thus three "dilutions" are dispensable via the valve assembly 10, the third dilution being provided by the invention without drastic change from the commercial valve assembly structures disclosed in the referenced U.S. Pat. Nos. 4,445,391 and 4,507,977, said valve assembly being capable of retrofit in substitution for one or the other of the last mentioned patented valve assemblies. This is accomplished despite the prior art teachings as to incorporation of means for providing such third dilution and notwithstanding the minimal available space in the aforementioned prior patented metering and transfer valve assemblies.

Figure 7:
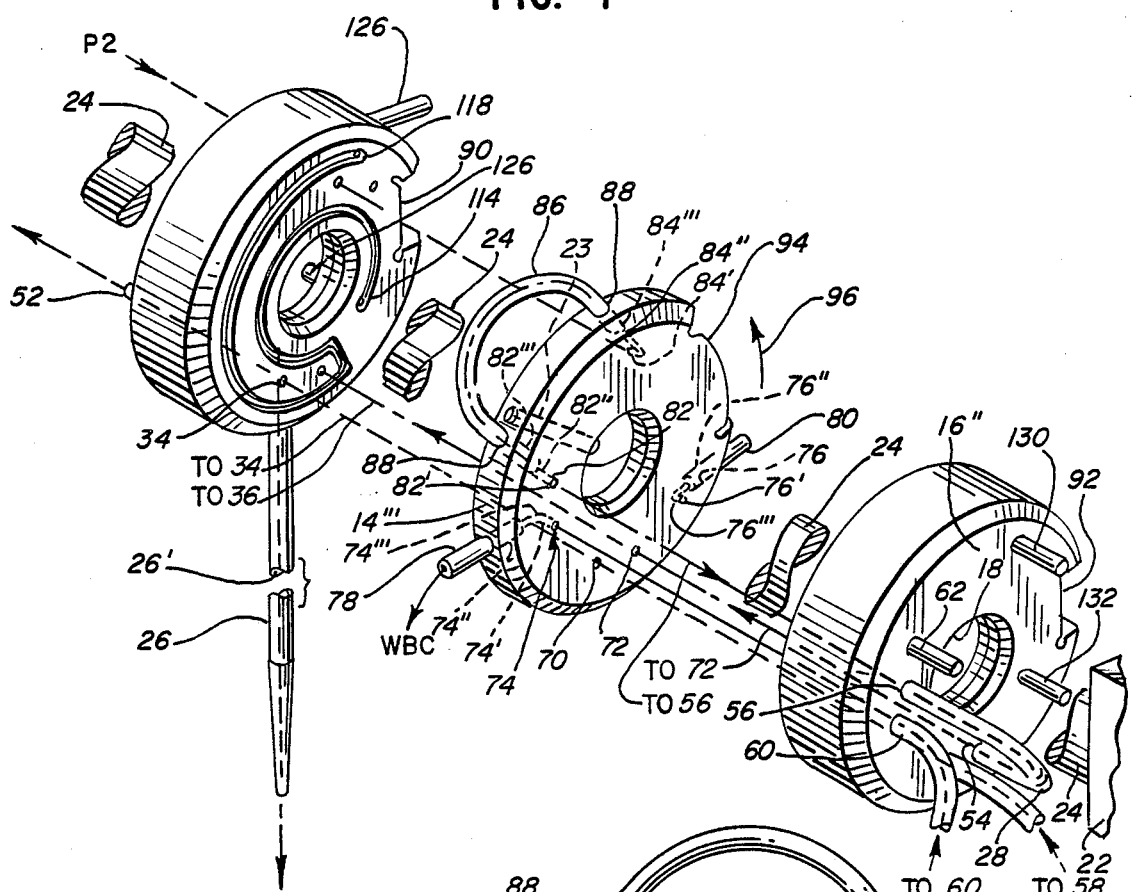
FIG. 7 is an exploded, diagrammatic, isometric representation of the liquid metering and transfer valve assembly of the invention illustrated in the condition assumed during the rinse or backwash mode of operation thereof; and, FIG. 8 is an enlarged elevational view of the center valve disc member of the valve assembly as shown in FIG. 7 showing one face thereof.
Figure 8:
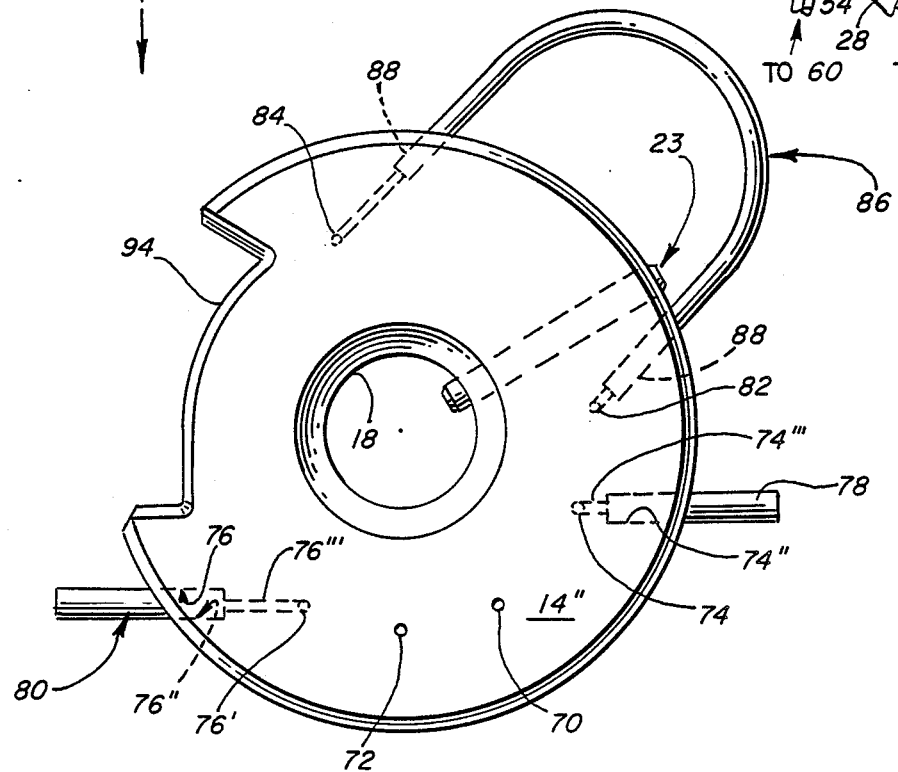

Referring now to FIG. 7, there is illustrated the provision, in the valve assembly 10, of means for rinsing or backwashing the said valve assembly subsequent to delivery therefrom of the measured volumes of liquid sample. The capability of the valve assembly to be so rinsed is a very important feature of the patented valve assemblies and must be provided in any commercial unit which incorporates the invention.

FIG. 7 represents the return of the valve assembly 10 from its delivery condition illustrated in FIG. 5 to the rinse or backwash condition or mode of operation. In FIG. 7, the central valve disc element 14 has been rotated from its disposition in FIG. 5 to its disposition in FIGS. 1 and 7 after the delivery mode of operation has been completed. In this rinse or backwash mode of operation, rinse liquid, generally the same as the diluent employed for diluting purposes, is delivered to the measuring portions of the valve assembly and the interior passageways employed to clear the same of residual liquid sample which may be therein. Other "cleaning" liquid may be employed to be followed by a rinse with the diluent liquid, the valve assembly remaining in the "rinse or backwash" condition.

The passageway 72, which carried a precisely measured volume of liquid sample and which sample had been delivered to the preselected destination location during the delivery mode of operation, now is disposed in communication with the passageways 54 and 36 of valve disc elements 16 and 12 respectively. Passageway 56 of valve disc element 16 is placed in communication with passageway 82 of the valve disc element 14. Passageway 84 of valve disc element 14 is disposed in communication with passageway 30 of valve disc element 12. Passageway 30 is coupled, by suitable conduit means (not shown) to the backwash or rinse pump P2 which is capable of directing cleaning liquid (or diluent) through the continuous path within the valve assembly 10 define by passageway 30, passageway 84, loop 86, passageway 82, passageway 56, loop 28, passageway 54, passageway 72, passageway 36 and the bore 26' of the aspirator probe 26 to a waste receptacle (not shown) exterior of the valve assembly 10. Thus a continuous path is defined through the valve assembly 10 for rinsing the measuring portions of said valve assembly. The remaining passageways 58, 70 and 34 are placed in series communication during the backwash mode of operation by coupling passageway 58 to said source of cleaning liquid or diluent. An additional backwash path is established to and through passageway 60, to and through passageway 74 to a location (not shown) exterior of the valve assembly 10. Thus any residual material in passageways 58, 70 and 34 is flushed to receptacles (not shown) exterior of the valve assembly 10 by suitable conduit means (not shown) coupled to passageway 34.

The herein invention not only provides a valve assembly 10 which is capable of delivering three dilutions employing only a single aspiration or loading step, and without drastic changes made to said patented valve assemblies provided by the U.S. Pat. Nos. 4,445,391 and 4,507,977, but in addition, incorporates means for preventing transmittal to the circumferential surfaces, of any material escaping from the junctions of the interior passageways at the frictionally engaged structures of said valve disc elements 12, 14 and 16, again without requiring drastic alteration of said patented structures and not withstanding the paucity of available space for such accommodation.

Accordingly, continuous channels 102 and 104 are formed in the faces 12" and 16' of valve disc elements 12 and 16 respectively. The channels 102 and 104 are generally uniform in cross-section and extend along the outer periphery of the said respective faces but spaced inwardly thereof, continuing in a radial direction along groove portions 102' and 104' respectively toward the central axis of the respective valve disc elements 12 and 16 to intersect with the groove portions 102" and 104" respectively formed in respective faces 12" and 16' of valve disc elements 12 and 16 along the inner periphery of passageway 18 thereof but spaced inward thereof.

An angular passageway 106 is formed in the valve disc element 12 and comprises a radial portion 108 extending inwardly from the circumferential surface 12'" to intersect with an axially parallel passageway portion 110 formed in the valve disc element 12 and opening to one end 112 of the channel 102. The intersection of radial portion 108 and axial portion 110 defines a generally right angle. An axially parallel passageway 114 also is formed in the valve disc element 12 extending from the face 12" thereof, inwardly to communicate with the opposite end 116 of the channel portion 102'", both passageway portion 110 and passageway 114 being parallel to the other axial passageways formed in said valve disc element 14. A pair of axially parallel through passageways 118 and 120 are formed in the valve disc element 16 opening to ends 122 and 124 of channel 104. Suitable nipples 126, 128, 130 and 132 are secured sealingly tightly within the passageway portion 108 and within passageways 114, 118 and 120 to establish communication with the exterior of the valve assembly 10 through respective surface 12'" and faces 12' and 16" respectively. The free ends of nipples 126, 128, 130 and 132 are coupled to suitable conduit means (not shown) leading to diluent (or cleaning liquid) dispensers (not shown) and suitable waste depositaries (not shown) so that any material which is deposited within the channels 102 and 104 can be flushed from the valve assembly 10. The respective channel portions 102' and 102'" are concentric one relative to the other; likewise, channel portions 104' and 104'" are concentric one relative to the other. The respective channel portions are concentric relative to the axial passageway 18 of the respective valve disc elements 12 and 16. The channels 102 and 104 isolate the openings of passageways 30, 34 and 36 to the face 12" of valve disc element 12 and of the openings of passageways 54, 56, 58, 60 and 62 to the face 16' of valve disc element 16 from the inner and outer periphery of said respective valve disc element. Thus liquid escaping from the junctions of the internal passageways of the valve assembly 10 at the frictionally engaged faces of said valve disc elements of said valve assembly cannot travel along said engaged faces and reach the circumferential surfaces of the assembled valve disc elements, having been intercepted by the respective channels 102 and 104. Of course, it should be noted that the portions of the surface of faces 14' and 14" which face the channels 102 and 104 respectively and are aligned with the opening portions thereof, are imperforate and thus seal said opening portions defining the respective channels.

It is believed apparent that variations in size, configuration and substitution of equivalents are capable of being made without departing from the spirit and scope of the invention as defined in the appended claims.

What we claim is:

1. A liquid metering and transfer valve assembly for use in a diluting system for providing at least three segmented, precise liquid samples from a single liquid sample source, at least two of said segmented liquid samples being of different volume, said valve assembly being operable between a loading condition and a delivery condition and including means for defining first, second and third segmenting portions in series communication with each other during the loading condition for receiving a continuous body of liquid sample from said source; said first, second and third segmenting portions being constructed and arranged to be isolated with the contents thereof one from the other; and there being means for combining each of said first, second and third isolated contents with a precise volume of diluent from a source of diluent and delivering said isolated contents with their associated amount of diluent to respectively different exterior locations; one of said segmenting portions being formed as first internal passageway means of precise internal volume, another of said segmenting portions formed as a first externally disposed hollow loop having a precise internal volume different from the internal volume of said first internal passageway means, and a second external hollow loop having a precise internal volume defining said third segmenting portion; second internal passageway means formed in said valve assembly and capable of establishing series communication with said first hollow loop and said first internal passageway means during the loading condition of said valve assembly and additional internal passageway means capable of being coupled to a source of diluent during the delivery condition of said valve assembly, said second external hollow loop being capable of isolating a precise volume of liquid sample therein and being disposed in communicating relationship with said additional internal passageway means during said delivery condition of said valve assembly for delivering its isolated volume of liquid sample with an associated amount of diluent to a preselected exterior location; whereby three precisely measured liquid sample volumes are measured and delivered to exterior locations along with respective precise volumes of diluent employing a single loading operation, said metering and transfer valve assembly being formed of a pair of spaced outer valve elements and an inner movable valve element sandwiched between said outer valve elements and coaxially aligned therewith, the valve elements having outer circumferential surfaces, each valve element having opposite faces and the opposite faces of the inner, movable valve element are sealingly frictionally engaged with the adjacent faces of the outer valve elements; the inner movable valve element carrying said first internal segmenting passageway means, one outer valve element carrying the first external hollow loop, and an aspirator probe secured to the other outer valve element being coupled to the liquid sample source; said additional internal passageway means for coupling said segmenting portions to the source of diluent being formed in both said outer valve elements; a pair of angular passageways formed in said inner valve element, said pair of angular passageways leading from angularly spaced apart locations along the outer circumferential surface of said inner valve element and opening to each face; said second external loop having opposite ends respectively secured to said outer circumferential surface of said inner valve element within respective ones of said angular passageways at said locations and extending outwardly of said outer circumferential surface.

2. The valve as claimed in claim 1 in which said additional internal passageway means comprises axial passageways formed in said outer valve elements.

3. The valve assembly as claimed in claim 2 in which there are a pair of axially parallel through passageways formed in said one stationary valve element which carries the aspirator probe, one end of one of said axially parallel through passageways is arranged to communicate with said second external hollow loop during the loading condition of said valve assembly, and one end of the other of said axially parallel through passageways is arranged to communicate with said second external hollow loop during the delivery condition of said valve assembly; the opposite end of the other of one of said parallel through passageways is arranged to communicate with a preselected exterior location in the delivery condition; aspirator pump means positioned exterior of said valve assembly, and said one of said axially parallel through passageways is arranged to communicate with said aspirator pump means during said loading condition of said valve assembly.

4. The valve assembly as claimed in claim 1 in which said additional internal passageway means comprise axial passageways formed in said outer valve elements and a second pair of angular passageways formed in said inner valve element, each one of said second pair of angular passageways opens from the outer circumferential portion of said inner valve element, is spaced angularly from said first pair of angular passageways and has its opposite ends opening to the face of said inner valve element; one of said second pair of angular passageways communicates with the exterior source of diluent and the other of said second pair of angular passageways is arranged to communicate with one end of said first external hollow loop, and the other of said second pair of angular passageways is arranged to communicate with the opposite end of said first external hollow loop.

5. The valve assembly as claimed in claim 4 in which there is an additional angular passageway formed in one of the outer valve elements, said additional angular passageway opens at one end thereof to the outer circumferential surface of said one of the outer valve elements, said aspirator probe is secured therein, the opposite end of said additional angular passageway opens to that face to that face of said outer valve element adjacent the face of said inner valve element, and, during the loading condition of said valve assembly, said opposite end is arranged to communicate with said first internal passageway means carried by said inner valve element and to one end of said first external loop.

6. The valve assembly as claimed in claim 1 in which said segmenting portions are arranged to be placed in non-common paths during delivery condition of said valve assembly.

7. The valve assembly as claimed in claim 1 in which said source of diluent includes separate dispenser means arranged each to feed preselected volumes of diluent to each of said segmenting portions, respectively, during the delivery condition of said valve assembly.

8. The valve assembly as claimed in claim 1 further including, continuous channel means formed in at least one of the faces of said outer valve elements which is frictionally engaged with the next adjacent face of said inner valve element; said channel means being spaced inwardly of the periphery of said one face and independent of the junctions of any of the internal passageways of said valve assembly; said channel means has an inlet, an outlet and bore means formed in that valve element carrying said channel means and communicating with said inlet and outlet and capable of being coupled to a source of rinse liquid, said channel means being capable of intercepting any material traversing said faces, said channel means being flushed by the rinse liquid of any material accumulating therein, the path taken by said rinse liquid being independent of other flow paths for liquid defined within said valve assembly.

9. The valve assembly as claimed in claim 8 in which said inlet is formed at the circumferential surface of its associated outer valve element, said bore means including a radial section communicating between the channel means and said inlet, said outlet being formed at an outer face of said associated valve element, said bore means further including an axially extending section communicating to said outlet.

10. In a liquid diluting and transfer valve assembly of the type which includes a pair of outer valve disc elements sandwiching an intermediate rotatable valve disc element, said valve disc elements being coaxially arranged and frictionally engagable face to face, the intermediate valve disc element having segmenting passageway means formed therein for measuring a first precise liquid sample volume, one of the outer valve disc elements having a first segmenting portion secured thereto for measuring a second precise liquid sample volume and the other of the outer valve disc elements carrying probe means capable of being disposed in communication with an exterior source of liquid sample, axial passageway means formed in the valve disc elements and arranged for establishing a series communication between the probe means, the segmenting passageway means and the segmenting portion during one condition of the valve assembly for establishing a continuous body of liquid sample therethrough and to establish independent paths through said valve assembly leading between the segmenting passageway means and the segmenting portion and locations exterior of said valve assembly, the segmenting portion formed as a first external loop having a precise internal volume; the improvement comprising, means for measuring a third precise liquid sample volume, said last mentioned means comprising a second external hollow loop secured to and extending outwardly from the outer circumferential surface of the intermediate valve disc element at a pair of angularly spaced locations along said outer circumferential surface, said second external loop having a precise internal volume and defining an additional segmenting portion for measuring said third volume, internal passageway means formed in said intermediate valve disc element and communicating with said second external hollow loop said second external loop and internal passageway means capable of being arranged in series communication with said first external loop and segmenting passageway means in one condition of said valve assembly so that the continuous body of liquid sample is included therein, said intermediate valve disc element arranged to be rotated to change the said valve assembly to a second condition and means to couple said second external loop and associated passageways to a source of diluent during said second condition and simultaneously segment the content of said second external loop from the continuous body of liquid sample within said continuous series path established during said one condition and deliver said contact to an externally located destination along a path independent of the other paths defined within said valve assembly whereby three precisely measured liquid sample volumes are measured and delivered to exterior destinations along with respective precise volumes of diluent employing single load condition of said valve assembly.

11. The valve assembly as claimed in claim 10 and continuous channel means formed in at least one of the faces of said outer valve disc elements which is frictionally engaged with the next adjacent face of said intermediate valve disc element; each of said channel means is spaced inwardly of the periphery of said one face and independent of the junctions of any of the internal passageways of said valve assembly, each of said channel means has an outlet, an outlet and bore means formed in each valve element carrying said channel means and communicating with said inlet and outlet; a source of rinse liquid; each of said channel means being capable of being coupled to the source of rinse liquid; said channel means being capable of intercepting any material traversing said faces and said channel means capable of being flushed by the rinse liquid of any material accumulating therein, the path taken by said rinse liquid being independent of other flow paths for liquid defined within said valve assembly.

12. The valve assembly as claimed in claim 11 in which the inlet of the channel means in one of the outer valve elements is formed on the circumferential surface of that element and said bore means associated therewith includes a radial portion communicating to the channel means carried by that element and the outlet associated therewith being formed at the outer face of that element and the bore means thereof including an axial portion communicating with that outlet.

* * * * *